United States Patent [19]

Lawson

[11] Patent Number: 4,640,267

[45] Date of Patent: Feb. 3, 1987

[54] METHOD AND APPARATUS FOR NONDETRIMENTAL REDUCTION OF INFANT CRYING BEHAVIOR

[76] Inventor: Philip A. Lawson, 5950-28 SW. 20th Ave., Gainesville, Fla. 32607

[21] Appl. No.: 706,086

[22] Filed: Feb. 27, 1985

[51] Int. Cl.$^4$ .............................................. A61B 5/00
[52] U.S. Cl. .................................................. 128/1 R
[58] Field of Search .............. 128/1 R, 1 D, 773, 905; 434/185; 178/31; 340/573-574

[56] References Cited

U.S. PATENT DOCUMENTS 4,093,821  6/1978  Williamson ..................... 128/773 X

OTHER PUBLICATIONS

Zicker, J. E. et al., "A Portable Microprocessor-Based Biofeedback Training Device", IEEE BME Trans., vol. 27, No. 9, Sep. 1980 pp. 509-515.

Primary Examiner—Lee S. Cohen
Assistant Examiner—Francis J. Jaworski
Attorney, Agent, or Firm—Cushman, Darby & Cushman

[57] ABSTRACT

A method and apparatus for conducting an operant conditioning paradigm designed to maintain the absence of vocal behavior, by a subject infant, which is equal to or above a predetermined audible level, thereby decreasing the probability of abusive behavior directed toward the subject infant by a parent or care provider. A specific schedule of reinforcement is utilized to maximize the effects of positive reinforcement, with the operation of the appropriate mode of the schedule of reinforcement being a function of the continuously monitored vocal behavior of the subject infant. A maintenance mode of said schedule of reinforcement includes the intermittent presentation of positive reinforcers, with the operation of said mode continuing indefinitely and independent of subject infant behavior until and unless the predetermined audible level is exceeded. A reacquisition mode of said schedule of reinforcement includes the contingent presentation of positive reinforcers, with the presentation of said positive reinforcers being contingent upon the cessation of vocal behavior which exceeds the predetermined audible level. A novel stimulus presentation mode is utilized to elicit a pause in vocal behavior which has exceeded the predetermined audible level for a predetermined period of time. An apparatus functioning per the present method may be enclosed in a unitary package adapted for attachment to a crib, playpen, or other appropriate child care device.

28 Claims, 6 Drawing Figures

METHOD AND APPARATUS FOR NONDETRIMENTAL REDUCTION OF INFANT CRYING BEHAVIOR

BACKGROUND OF THE INVENTION

An electronic apparatus functioning per the present method is usable with an infant or young child to reduce (without harm to the infant or child) vocal behavior by the subject child which is equal to or above a predetermined audible level. Such pacification reduces the probability of an abusive attack against the subject child by a potentially abusive parent or care provider.

Child abuse by parents or care providers is a major problem of virtually epidemic proportion which is currently receiving pervasive coverage throughout the mass media. Additionally, many studies have sought to define the problem from a statistical viewpoint. For example, the American Humane Association indicates that (with only thirty-six states reporting) there were 223,034 reports of physical child abuse in the United States alone during 1982. The Federal Bureau of Investigation has estimated that as many as 5,000 children died as a result of such abuse during this time period. Longterm emotional trauma as well as permanent physical disability are worst-case possibilities for an abused child, where death does not occur. Moreover, abused children are likely to grow up to abuse their children or others, thereby perpetuating the problem. Further, there is general agreement among researchers and other experts in the field that reported figures for physical child abuse in a given time period are, in reality, a gross underrepresentation of the actual number of such abusive incidences.

Despite overwhelming evidence and pervasive social recognition of the child abuse problem, effective solutions have not been forthcoming.

It is recognized, however, that the act of "crying" is the single behavior, emitted by children or infants, which is most likely to be present in abusive attacks on children by their parents or care providers. Actual laboratory experiments have demonstrated that infant "crying" can function as a stimulus which gives rise to abusive parental behavior directed toward children.

OBJECTS AND SUMMARY OF THE INVENTION

It is an object of the present invention to attenuate the occurrence of those infant "crying" behaviors associated with abusive attacks on infants by their parents or care providers. Utilizing a positive reinforcement paradigm, the subject technology will—absent distress—pacify "crying" infants. Such pacification will thereby decrease the probability of such abusive attacks, i.e., if an infant "cries" less, there is a decreased probability of such abusive attacks. An additional benefit of the subject technology involves the issue of infant stimulation, i.e., said positive reinforcement paradigm provides an infant with an interesting, entertaining environment. Such stimulation is generally accepted to be a factor critical to optimal infant development.

This invention focuses on the nondetrimental reduction of exhibited "crying" behavior of infants or young children. A criterion response (R) is established, with such criterion response being defined as vocal behavior equal to or above a predetermined audible level (i.e., threshold TH). Accordingly, in one form, the present invention essentially maintains the absence of the criterion response (i.e., the absence of vocal behavior which is equal to or above the threshold TH).

In the event that the subject child emits vocal behavior which is equal to or above the threshold TH, such behavior is not dealt with in a detrimental fashion. The entire focus of this invention and the chief concern of the present inventor are the safety and well-being of the subject children. Accordingly, it would be totally repugnant to the very purpose of the present inventor to inflict any detrimental measures upon a child or infant.

The present invention utilizes positive reinforcement to maintain the absence of the criterion response (i.e., the absence of vocal behavior which is equal to or above the threshold TH).

Various stimuli have been used in attempts to pacify "crying" children, and thereby minimize such "undesirable" behavior. One well-known example is the use of placental sounds, including a mother's heartbeat, to comfort a "crying" child.

However, the problem of satiation (or habituation) occurs when such stimuli (i.e., "reinforcers") are presented continuously and noncontingently. That is, the continued presentation or availability of a reinforcer reduces its effectiveness. Accordingly, infants to whom such "reinforcers" are presented continuously and noncontingently become satiated with respect to the calming effects of such "reinforcers."

The present invention mitigates the problem of satiation (as well as other problems) present in prior attempts at reducing the "crying" behavior of infants or young children. A specific schedule of reinforcement is utilized. Several breakpoints (i.e., changes) divide the schedule into different modes, with the operation of the appropriate mode being a function of the continuously monitored vocal behavior of the subject child.

If the presentation of a stimulus as a consequence of a response results in an increased probability that the response will recur in the future, the stimulus is referred to as a positive reinforcing stimulus or a positive reinforcer. With respect to the present invention, a given reinforcer presentation may be comprised of any one of a variety of positive reinforcers or various combinations thereof.

If a stimulus does in fact consequate (i.e., occurs as a consequence of) a response—although it need not do so to have an effect—the consequence is said to be contingent upon the response. The specific contingency under which reinforcements are assigned to particular responses is referred to as the schedule of reinforcement, and a specific such schedule and selected portions thereof comprise some of the features of the present invention.

For example, during initial operation of one apparatus in accordance with the present invention, if the child is not emitting the criterion response, a defined mode 1 operation will conduct a variable time (VT) schedule of stimulus ("reinforcer") presentations (i.e., mode 1 presents "positive reinforcers" at variable or intermittent time intervals). Operation of mode 1 continues indefinitely and independent of subject child behavior until and unless the child emits the criterion response. In this event, mode 1 operation is suspended, and a defined mode 2 operation (discussed further below) is engaged.

Given that mode 1 presents "positive reinforcers" at variable time intervals regardless of subject child behavior, it should be noted that this use of the term "reinforcer" is broader than the foregoing definition. Indeed, the presentation of "reinforcers" under the mode 1 schedule is not contingent upon any response by the subject child. However, this use of the term is commonplace, to the extent that the temporal contiguity (i.e., close proximity in time) existing between the occurrence of behavior and the presentation of such "reinforcers" is known, under some circumstances, to maintain or accelerate such behaviors. Therefore, with respect to the present invention, such incidental reinforcement may function to maintain or accelerate behaviors which are incompatible with the criterion response, thereby maintaining the absence of vocal behavior which is equal to or above the threshold TH.

For example, the threshold level TH may be set so that cooing and babbling, vocal behaviors which are generally accepted as essential to the development of language, will not constitute a criterion response (i.e., vocal behavior which is equal to or above the threshold TH). Therefore, such behaviors may freely occur under the variable time (VT) schedule of mode 1. That is, during mode 1 operation, the presentation of a designated "reinforcer" R1 will, on occasion, be temporally contiguous (i.e., close in time) with the occurrence of cooing and babbling behavior. However, the relationship between the occurrence of such behaviors and the presentation of such "reinforcers" is purely incidental (i.e., random), rather than contingent. Nevertheless, the incidental reinforcement of such behaviors may advantageously serve to accelerate those behaviors associated with language acquisition.

Defined mode 1 presents "reinforcers" on an intermittent basis, so that the satiation effects discussed above can be attenuated. One useful function of mode 1 is to facilitate the efficacy of the "reinforcers" utilized therein as "legitimate" reinforcers in defined mode 2. Specifically, if the subject child emits the criterion response (i.e., vocal behavior equal to or above the threshold TH), such response may result, in one form of the invention, in a suspension or time out (TO) from mode 1 operation in favor of mode 2 operation.

In mode 2, the presentation of a reinforcer is contingent upon cessation of the criterion response for a predetermined period of time, which criterion response resulted in the above-described initial change from mode 1 operation to that of mode 2 operation. Such a schedule of reinforcement may be denoted as ($\bar{R}>t$), i.e., the non occurrence of the criterion response (R) for a predetermined period of time (t). Since in a ($\bar{R}>t$) schedule not emitting a particular response is treated as if it were a response, reinforcement in manifested by a decrease in the criterion response (i.e., a decrease is vocal behavior equal to or above the threshold TH). Contingent upon the cessation of the criterion response for a predetermined period of time, mode 2 presents a positive reinforcer for a limited, predetermined period of time to once again mitigate satiation effects. However, note that such reinforcer presentation may be preselected so as to be comparatively long with respect to the overall distribution of "reinforcer" presentations on the (VT) schedule. The absence of the criterion response for such period of time constitutes successful retraining of the subject child (i.e., reduction of "crying" behavior), and results in a return to the (VT) schedule of mode 1, discussed above.

BRIEF DESCRIPTION OF THE DRAWINGS

The foregoing disclosure is an overview of select attributes and features of the present invention, with the specific features thereof fully disclosed in the following description with reference to FIGS. 1-4, wherein.

DESCRIPTION OF THE PREFERRED EMBODIMENTS

Figure 1:
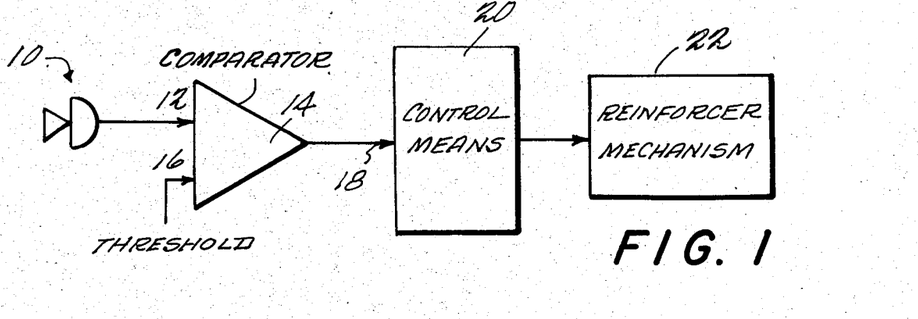
FIG. 1 is a functional block diagram of an exemplary apparatus of the minimum elements necessary to perform the presently disclosed invention.

Referring to FIG. 1, an audio input device represented by microphone 10 is used to monitor the vocal behavior of the subject child. The signal produced by microphone 10 constitutes an input 12 for comparator 14. Comparator 14 has another input 16, a predetermined audible threshold TH, which input is used for comparison with the signal at input 12 to determine the presence or absence of subject vocal behavior equal to or above the threshold TH. The result of this comparison is input at 18 to logic circuitry, generally represented by control means 20.

The presence or absence of the criterion response (i.e., vocal behavior equal to or above the predetermined threshold TH) is the only external data gathering necessary, with regard to the behavior of the subject child, for implementation of the schedule of reinforcement in accordance with the present invention. Thus, the control means 20 may be comprised of a microprocessor device programmed in accordance with the methodology discussed further below, or control means 20 may be comprised of a hard-wired device accomplishing the same. Specific selection of the precise physical embodiment of the control means 20 is subject to the design choice of one of ordinary skill in the art, and such choice may be dependent upon various factors, such as cost and size optimization, which are not the major areas of concern for the broader teachings of the present invention. A functional apparatus, however, operating per the present method is a feature of the present invention, as recited in the appended claims.

Implementation of the present methodology may be accomplished by a microprocessor device acting upon the comparator output 18, with such device controlling a reinforcer mechanism 22. Reinforcer mechanism 22 may incorporate a cassette tape player or other device which replays specific sounds, or sequences thereof, which constitute positive reinforcers. These may include, for example, recordings of placental sounds or maternal heartbeats, as discussed above. However, any audible positive reinforcer may be used.

Alternatively, the reinforcer mechanism 22 may be specific lights or moving objects which present kaleidoscopic or patterned stimuli to the subject child in a fashion which constitutes a positive reinforcer. Further exemplary reinforcer mechanisms may include physical structures (such as mobiles) which are controllably moved, rotated, or provided with some other motion in a fashion which constitutes a positive reinforcer. Motion-causing devices (such as rockers or vibrators for a crib) are also optionally usable as the reinforcer mechanism 22 of the present invention. Various selective combinations of any of the foregoing exemplary reinforcer mechanisms are also within the scope of the present invention, as discussed further below with regard to FIG. 2.

The entire physical apparatus of FIG. 1 may be self-contained and battery operated in a relatively small package. Such packaging technique would permit association of such a device with an existing child care device such as a playpen or crib. Such packaging may also be adapted for attachment to other existing child care devices such as a highchair, walker, or stroller, etc. In any event, an apparatus in accordance with the present invention is adapted to desirably interface with the given environment of the subject child.

Figures 2, 4:
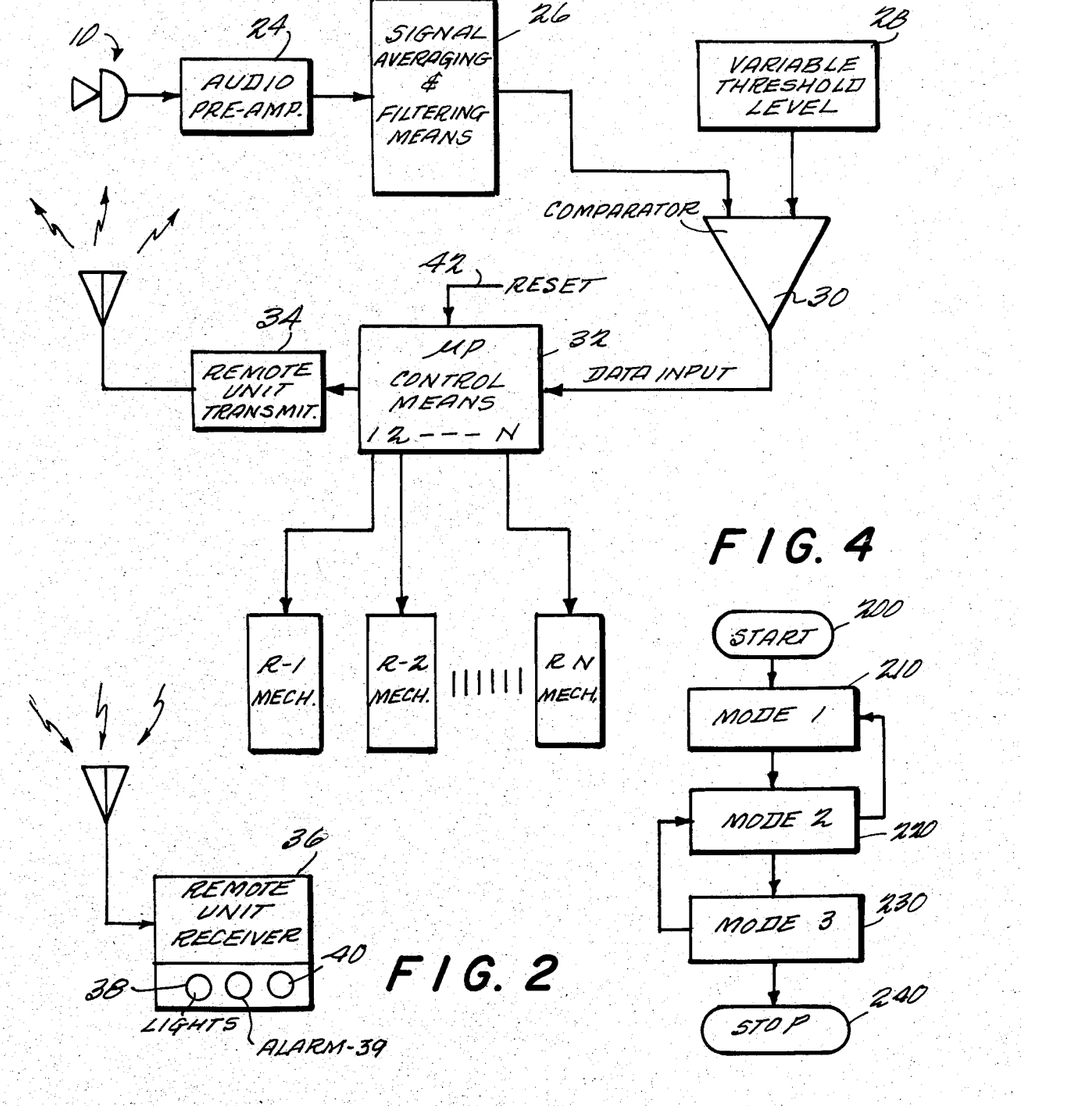
FIG. 2 is a second embodiment of an exemplary apparatus which additionally includes some optional features of the present invention.
FIG. 4 is a general flow diagram disclosing the interrelationships of three (3) exemplary modes functionally related to subject child behavior in accordance with the methodology of the present invention.

The apparatus disclosed in FIG. 2 additionally includes certain other optional features of the present invention which may be utilized in conjunction with an "advanced" version of the basic exemplary embodiment of FIG. 1.

Referring to FIG. 2, element 10, once again, represents a microphone device for pickup of the vocal behavior of the subject child. It is to be understood that this device may be any suitable microphone which is appropriately incorporated into the surface of the structure of the FIG. 2 apparatus or remotely attached thereto by necessary wires. However, such pickup may be alternatively achieved by a wireless connection between the microphone device and the FIG. 2 apparatus.

Audio preamplifier 24 may be optionally associated with the output of the microphone 10 to establish a proper (i.e., buffered) signal for ultimate comparison with the threshold TH. Signal averaging and filtering means 26 (conventional devices ) may be associated with the output of audio preamplifier 24 to provide improved signal acquisition for comparison with the threshold TH.

The threshold TH itself may be variable as shown by element 28. Variability of the threshold TH may be achieved through any number of conventional approaches, including use of a variable potentiometer or a variable resistor with a fixed voltage input.

The output signal of the signal averaging and filtering means 26 is compared with the established variable threshold TH from 28 in the comparator 30. Comparator 30 is essentially equivalent to comparator 14 of FIG. 1. Thus, the data which are input to the control means 32 again need only be indicative of the presence or absence of the criterion response (i.e., vocal behavior equal to or above the variable threshold TH), as established by 28.

The control means 32 is represented in this exemplary embodiment as a microprocessor having data input from comparator 30 and having a plurality of peripheral outputs. These outputs are represented by 1, 2, . . . , N and control reinforcer mechanisms R1, R2, . . . , RN, respectively. As discussed above, these mechanisms may be of any variety and type which constitute positive reinforcers for human subjects in their infancy or early childhood.

Economic considerations and applicability to differing environmental settings are considerations in the selection of particular reinforcer mechanisms. For example, a particular embodiment, such as one designed for a crib or playpen, may have a rocker or vibrator reinforcer mechanism associated with it, while such rocker or vibrator reinforcer mechanism would not be practical for a stroller, walker, or highchair. Specific selection of a reinforcer mechanism or combinations thereof thus depends on applicability of the present invention to a particular environmental setting, and such selection therefore need not form a limitation of the general teachings of the present invention.

The remote unit transmitter 34 of FIG. 2 enables the control means 32 to send data to a remote location, with such data being detected by remote unit receiver 36. This component of the present apparatus enables the parent or care provider to remotely identify the particular mode or phase of the schedule of reinforcement currently in operation. Remote unit receiver 36 incorporates lights 38 and 40 and alarm 39, which are exemplary of indicator outputs which may be used with such a remote unit receiver.

In addition to the convenience of this feature, there is the additional advantage of enabling the parent or care provider to avoid unwittingly reinforcing "undesirable" behavior. For example, the pickup of a particular transmitter signal as detected by the remote unit receiver and represented by the operation of green indicator light 38 may signify that the mode 1 schedule is in operation. Such a signal would indicate successful maintenance of the absence of the criterion response. Moreover, such a signal would alert the parent or care provider to the desirability of entering the subject child's room to present additional positive reinforcers, especially those that an inanimate entity is incapable of providing (e.g., hugs, kisses, and so on).

Operation of red indicator light 40 may signify that the mode 2 schedule of reinforcement or other appropriate mode (i.e., mode 3 discussed further below with regard to FIG. 3C) is in operation. Such a signal would indicate that the subject child has emitted the criterion response and that the subject child is currently being retrained with respect to the reduction of such behavior. Furthermore, in the absence of actual distress, such a signal would alert the parent or care provider to the undesirability of entering the subject child's room, thereby avoiding the differential reinforcement of "undesirable" behavior. However, operation of alarm 39 may be defined to signify that the subject child has been emitting the criterion response for a predetermined period of time. Thus, operation of alarm 39, by one definition, may be indicative of a high probability of actual distress, requiring immediate intervention by a parent or care provider.

Both devices (transmitter 34 and receiver 36) may be any paired conventional devices permitting wireless communication of digital data (e.g., "yes" or "no" data for a particular indication) over a relatively short distance. Their particular embodiments are not intended as novel features of the present invention. Additional lights, audible signals, or other indicators may be included for indicating other defined modes or phases of the schedule of reinforcement.

Reset input 42 of the microprocessor 32 provides a convenient and efficient mechanism for restarting the apparatus, e.g., after a period of parental or care provider intervention. A parent or care provider who interrupts the operation of the apparatus may use the reset feature of the microprocessor to clear vocal behavior data which may have suspended the operation of the apparatus in accordance with the methodology of the present invention, as discussed below. For example, introduction of the "alarm" operation, discussed above, may also be accompanied by subsequent suspension of the operation of the apparatus. In such an instance, a parent or care provider can intervene to "manually" assist the subject child until criterion responding ceases. Use of reset button 42 enables the FIG. 2 embodiment to resume operation under the appropriate mode of the schedule of reinforcement.

Figure 3A:
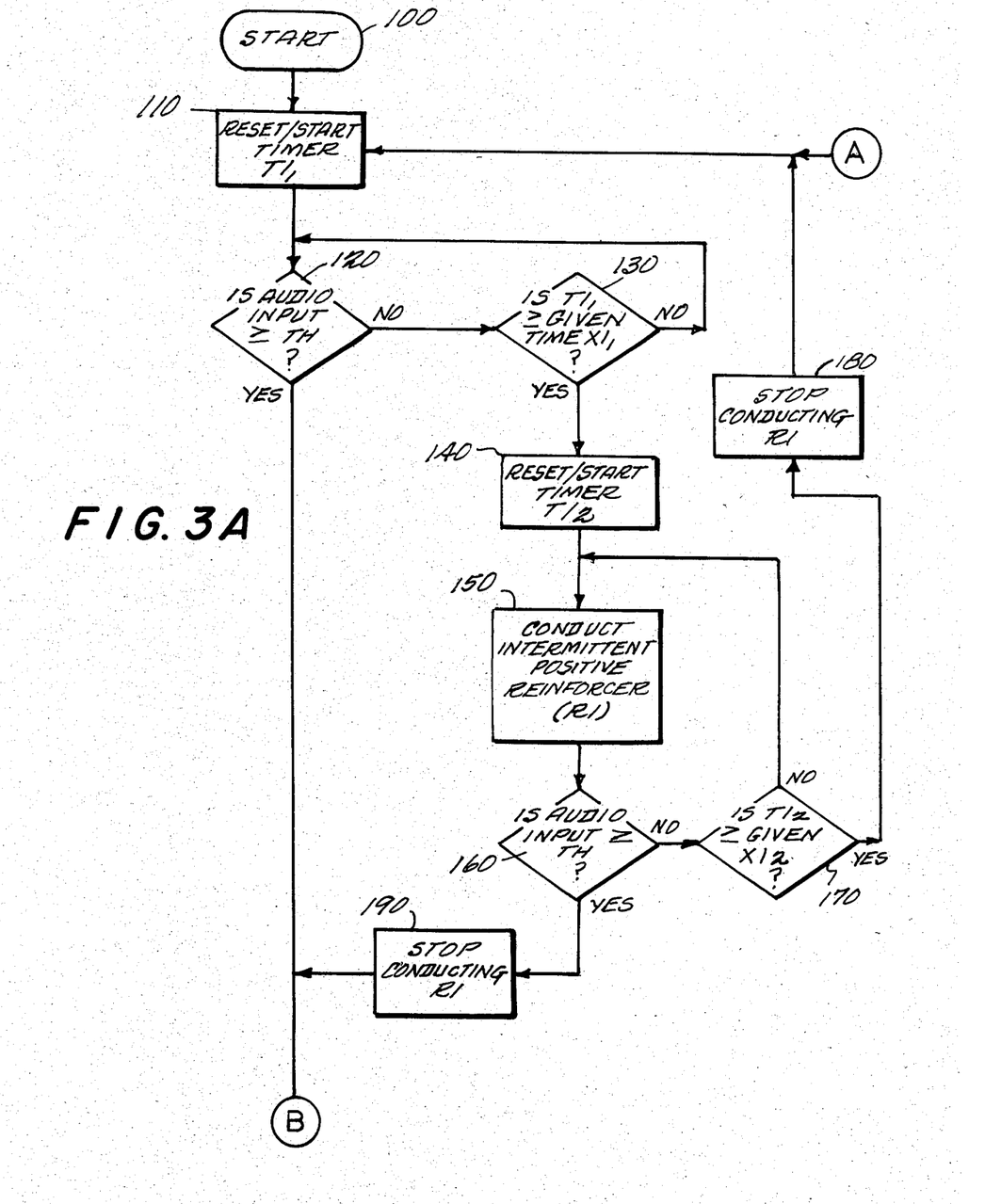
FIGS. 3A through 3C are a flow chart describing the present methodology, including an exemplary schedule of reinforcement in accordance therewith.
Figure 3B:
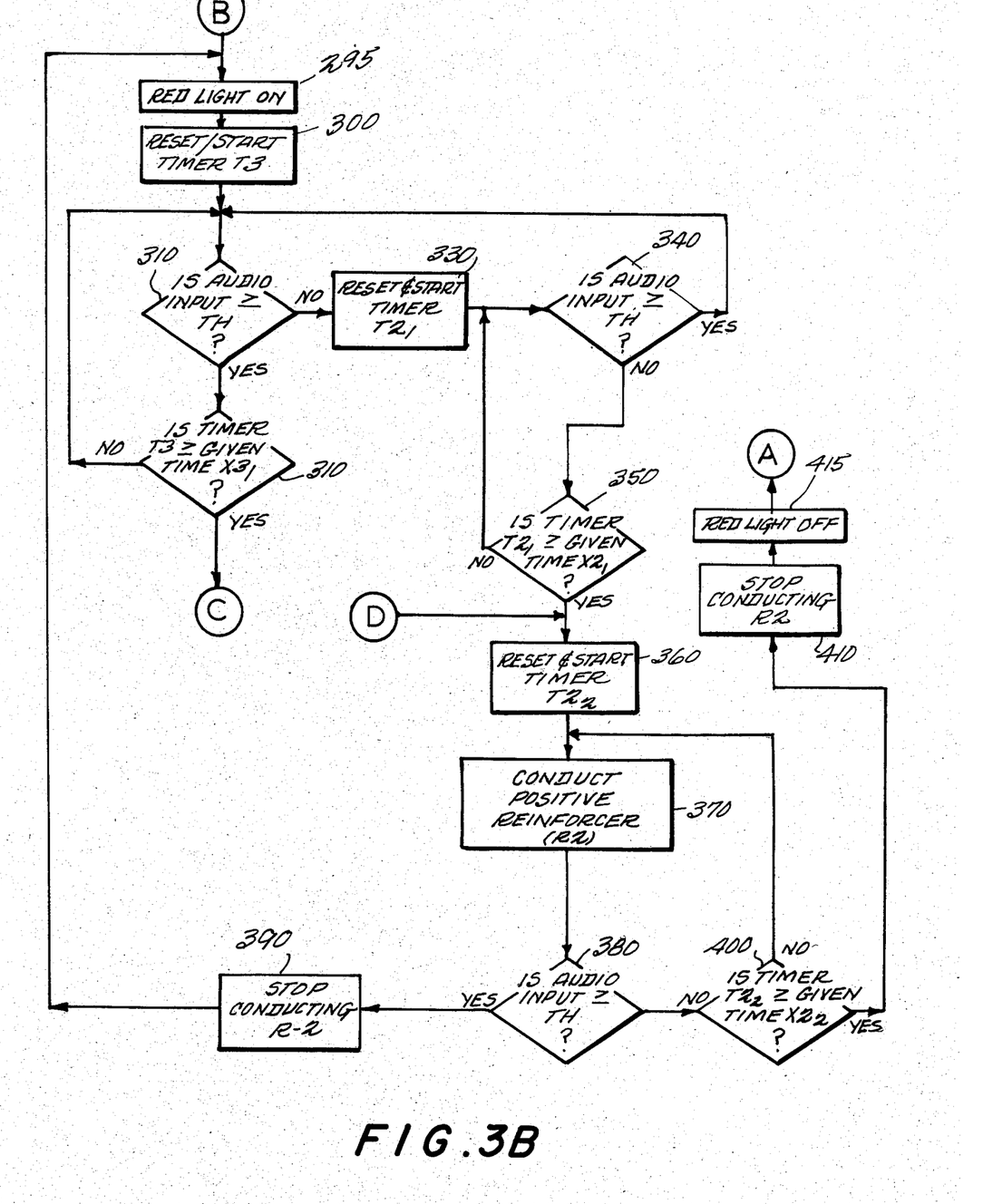
Figure 3C:
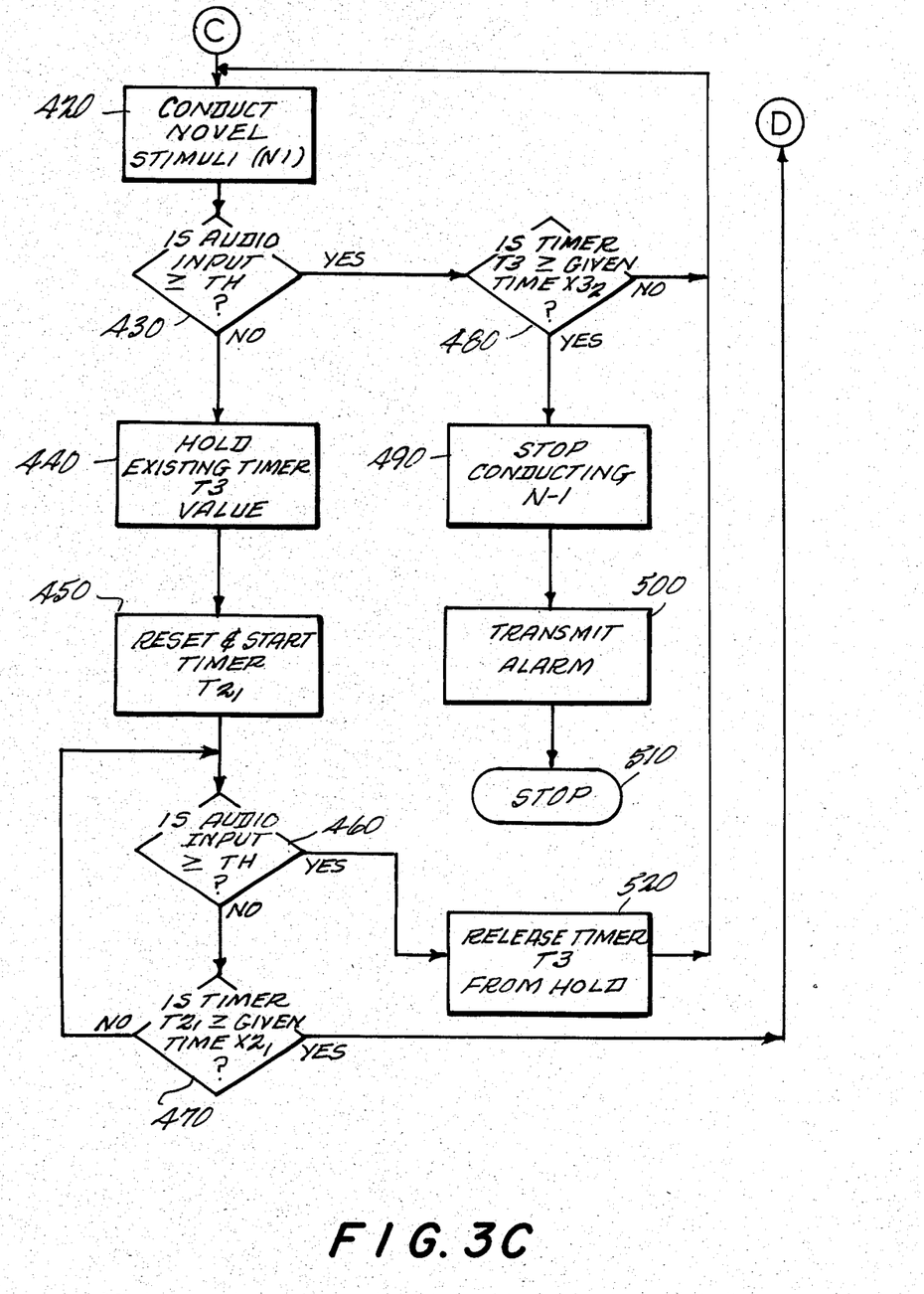

With regard to the methodology of operation of control means 20 (of FIG. 1) and microprocessor control means 32 (of FIG. 2), FIGS. 3A-3C fully outline, in flow chart format, the salient features of the present method.

The present method utilizes a number of different timing sequences to determine the appropriate mode of the schedule of reinforcement, as a function of the continuously monitored vocal behavior of the subject child. The flow chart of FIGS. 3A-3C delineates a number of different timers, each usually associated with a given time period for comparison therewith, to determine appropriate reinforcer conduct. Each of these given time periods is usually variable, although any of such given time periods may be preselected in a particular embodiment, or any of such given time periods may be randomly selected by a probability generator or other device accomplishing an analogous function.

Referring to FIG. 3A, start 100 may be associated either with the initial start operation for an apparatus of a FIGS. 1 or 2 embodiment, or with the reset operation 42 of the microprocessor 32 of FIG. 2. In either event, timer $T1_1$ is reset and started in step 110. Timer $T1_1$ times the duration during which the subject child does not emit the criterion response (i.e., vocal behavior equal to or above the threshold TH).

Decision branch 120 tests to determine if the audio input level (i.e., the vocal behavior of the subject child) is equal to or above the threshold TH. If the subject child emits vocal behavior equal to or above the threshold TH, a "YES" branch (i.e., branch "B") is taken from decision branch 120 to FIG. 3B, wherein mode 2 operation is engaged. If the subject child is not emitting the criterion response, a "NO" branch is taken from decision branch 120, and a "loop" is established around decision branch 130, where the elapsed time $T1_1$ is compared with the given time $X1_1$. This is the first instance of comparison between a timer and a given time, as alluded to earlier. Also, it should be noted that monitoring of subject child vocal behavior is actually continuous, although the flow chart indicates that such monitoring is acted on discretely.

$X1_1$ is the given time (i.e., the duration during which the subject child does not emit the criterion response) required for the presentation of "reinforcer" R1. When the elapsed time $T1_1$ is equivalent to or in excess of the given time $X1_1$ a "YES" branch is taken from decision branch 130 to step 140, where timer $T1_2$ is reset and started. Timer $T1_2$ times the duration of the "positive reinforcer" R1 presentation, as conducted in step 150, which presentation is a function of the variable time (VT) schedule of mode 1 (i.e., timer $T1_1$ compared with the given time $X1_1$ causes the presentation of the "positive reinforcer" R1 to be conducted on the variable time (VT) schedule of mode 1—only in the absence of the criterion response).

Decision branch 160 tests for continued absence of the criterion response. In the continued absence of the criterion response, a "NO" branch is taken from decision branch 160, and a "loop" is established around decision branch 170, where the elapsed time $T1_2$ is compared with the given time $X1_2$. $X1_2$ is the given time that the "positive reinforcer" R1 is presented in the continued absence of the criterion response. When the elapsed time $T1_2$ is equivalent to or in excess of the given time $X1_2$, a "YES" branch is taken from decision branch 170 to step 180, where the presentation of "positive reinforcer" R1 is suspended. Upon the conclusion of step 180, timer $T1_1$ is reset and started in step 110. Such an affirmative decision in decision branch 170 causes a continuation of the variable time (VT) schedule of mode 1.

It should be noted, however, that if the subject child emits vocal behavior equal to or above the threshold TH before $T1_2$ is equivalent to or in excess of $X1_2$, a "YES" branch is taken from decision branch 160 to step 190, where the presentation of "positive reinforcer" R1 is suspended. Upon the conclusion of step 190, branch "B" is taken to FIG. 2B, wherein mode 2 operation is engaged.

From the foregoing overview of FIG. 3A, it may be seen that the operation of mode 1 is characterized by the subject child not emitting the criterion response, resulting in the intermittent presentation of "positive reinforcer" R1 in accordance with the variable time (VT) schedule thereof.

Referring to FIG. 4, the start position 200 corresponds to the start position 100 of FIG. 3A. Exit from mode 1 to mode 2 (i.e., 210 to 220 in FIG. 4) corresponds to exit, via branch "B", from the affirmative branches of decision branches 120 and 160 of FIG. 3A. If the affirmative branch from decision branch 120 is taken, either the "positive reinforcer" R1 was not being conducted or step 180 had suspended such conducting. If the affirmative branch from decision branch 160 is taken, step 190 suspends the conducting of "positive reinforcer" R1. In either case, operation of the mode 1 schedule [i.e., (VT)] is suspended and branch "B" is taken to FIG. 3B, wherein mode 2 operation is engaged. Thus, the (VT) schedule is suspended because the subject child is emitting the criterion response.

Referring to FIG. 3B, it is known by definition (i.e., an affirmative decision in decision branch 120 or 160) that the subject child is emitting the criterion response (i.e., vocal behavior equal to or above the threshold TH. Accordingly, in step 295, the "RED LIGHT ON" signal (discussed above with regard to elements 34, 36, and 40 of FIG. 2) is transmitted simultaneously with the reset and start of timer T3 in step 300. Timer T3 times the duration during which the vocal behavior of the subject child is equal to or above the threshold TH. Decision branch 310 tests to determine if the audio input level (i.e., the vocal behavior of the subject child) is equal to or above the threshold TH. If the subject child continues to emit vocal behavior equal to or above the threshold TH, a "YES" branch is taken from decision branch 310 and a "loop" is established around decision branch 320 until the elapsed time T3 is equivalent to or in excess of the given time $X3_1$. When such event occurs, a "YES" branch (i.e., branch "C") is taken from decision branch 320 to FIG. 3C, wherein mode 3 operation (discussed further below with regard to FIG. 3C) is engaged. However, as long as the timer T3 "loop" is operative, mode 2 is engaged, so that only positive reinforcer R2 can be presented, if any stimulus presentation is conducted.

The presentation of positive reinforcer R2 is contingent upon the behavior of the subject child. Specifically, the presentation of positive reinforcer R2 is contingent upon the cessation of the criterion response for a predetermined period of time. Therefore, upon cessation of the criterion response, a "NO" branch is taken from decision branch 310 to step 330, where timer $T2_1$ is reset and started. Timer $T2_1$ times the duration during which the subject child does not emit the criterion response, after mode 2 (i.e., FIG. 3B) has been entered.

Decision branch 340 tests for continued absence of the criterion response. In the continued absence of the criterion response, a "NO" branch is taken from decision branch 340, and a "loop" is established around decision branch 350, where the elapsed time $T2_1$ is compared with the given time $X2_1$. $X2_1$ is the given time (i.e., the duration during which the subject child does not emit the criterion response) required for the presentation of positive reinforcer R2. When the elapsed time $T2_1$ is equivalent to or in excess of the given time $X2_1$, positive reinforcer R2 is presented.

It should be noted, however, that if the subject child emits the criterion response (i.e., vocal behavior equal to or above the threshold TH) after a cessation of such behavior but before $T2_1$ is equivalent to or in excess of $X2_1$, a "YES" branch is taken from decision branch 340, which causes a return to the input of decision branch 310. Such affirmative decision in decision branch 340 causes a suspension of the current operation of timer $T2_1$.

Referring again to decision branch 350, if the "YES" branch of decision branch 350 is taken, timer $T2_2$ is reset and started in step 360. Timer $T2_2$ times the duration of the positive reinforcer R2 presentation, as conducted in step 370.

Decision branch 380 tests for continued absence of the criterion response. In the continued absence of the criterion response, a "NO" branch is taken from decision branch 380, and a "loop" is established around decision branch 400, where the elapsed time $T2_2$ is compared with the given time $X2_2$. $X2_2$ is the given time that the positive reinforcer R2 is presented, contingent upon the continued absence of the criterion response. When the elapsed time $T2_2$ is equivalent to or in excess of the given time $X2_2$, a "YES" branch is taken from decision branch 400 to step 410, where the presentation of positive reinforcer R2 is suspended simultaneously with the transmission of the "RED LIGHT OFF" signal (as discussed above with regard to elements 34, 36, and 40 of FIG. 2) in step 415, which causes a return, via Branch "A", to the reset and start of timer $T1_1$ in step 110 of FIG. 3A. That is, successful retraining of the subject child (i.e., cessation of the criterion response for the given time $X2_2$) causes a reversion from mode 2 operation to mode 1 operation (i.e., from FIG. 3B to FIG. 3A).

It should be noted, however, that if the presentation of positive reinforcer R2 does not result in the cessation of the criterion response for the given time $X2_2$, a "YES" branch is taken from decision branch 380, which suspends presentation of positive reinforcer R2 in step 390 and causes a return to the reset and start of timer T3 in step 300 [i.e., the initial starting point of mode 2 operation (FIG. 3B)]. Therefore, continued operation of mode 2 may result either in a reversion to mode 1 operation (i.e., FIG. 3A) or a transfer "downward" to mode 3 operation (i.e., FIG. 3C), as previously described with regard to branch "C" of decision branch 320 of FIG. 3B.

Referring again to FIG. 4, the interrelationship existing between mode 2 and modes 1 and 3 is displayed diagrammatically therein. That is, mode 2 (220) may result either in a reversion to mode 1 operation (210) or a "transfer" to mode 3 operation (230).

Referring to FIG. 3C, mode 3 operation is engaged if the subject child continues to emit vocal behavior equal to or above the threshold TH for the given time $X3_1$ (i.e., an affirmative decision in decision branch 320 of FIG. 3B), after entering mode 2. $X3_1$ is the given time during which the subject child continues to emit vocal behavior equal to or above the threshold TH without a pause of sufficient duration to allow for the presentation of positive reinforcer R2 in accordance with the ($\overline{R} > t$) schedule of mode 2. Mode 3 operation utilizes the presentation of novel stimuli N1 in an attempt to elicit an "orienting response" which will result in a pause in such vocal behavior of sufficient duration to cause a reversion to mode 2 operation.

Step 420 presents novel stimuli N1, which stimuli may be any suitable nondetrimental audio or visual stimuli, such as flashing lights or brief audible stimuli. After the presentation of novel stimuli N1 in step 420, decision branch 430 tests to determine if the audio input level (i.e., the vocal behavior of the subject child) is equal to or above the threshold TH. In the absence of the criterion response, the "NO" branch of decision branch 430 is taken to step 440, where the existing time T3 is held, so that timer $T2_1$ may be reset and started in step 450.

As discussed above (i.e., mode 2 of FIG. 3B), timer $T2_1$ times the duration during which the subject child does not emit the criterion response. Decision branch 460 tests for continued absence of the criterion response. In the continued absence of the criterion response, a "NO" branch is taken from decision branch 460, and a "loop" is established around decision branch 470, where the elapsed time $T2_1$ is compared with the given time $X2_1$. $X2_1$ is the given time (i.e., the duration during which the subject child does not emit the criterion response) required for the presentation of positive reinforcer R2. When the elapsed time $T2_1$ is equivalent to or in excess of the given time $X2_1$, a "YES" branch (i.e., branch "D") is taken from decision branch 470 to step 360 of FIG. 3B, where mode 2 operation resumes with the presentation of positive reinforcer R2.

Referring again to decision branch 460, if the subject child emits vocal behavior equal to or above the threshold TH after the absence of such behavior is determined in decision branch 430, a "YES" branch is taken from decision branch 460 to step 520, where timer T3 is released from the "hold" put thereon in step 440. Upon the conclusion of step 520, the presentation of novel stimuli N1 resumes in step 420.

Referring once again to FIG. 4, an affirmative decision in decision branch 470 of FIG. 3C corresponds to a reversion from mode 3 (230) to mode 2 (220) in FIG. 4. Mode 3 operation ultimately causes either a reversion to mode 2 operation (which may, in turn, result in a reversion to mode 1 operation) or a "stop" at step 240.

It should be noted, however, that if the presentation of novel stimuli N1 in step 420 does not result in a pause in vocal behavior equal to or above the threshold TH of sufficient duration to cause a reversion to mode 2 operation, a "YES" branch is taken from decision branch 430 and a "loop" is established around decision branch 480, where the elapsed time T3 is compared with the given time $X3_2$. $X3_2$ is the given time required for a given number of novel stimulus N1 presentations. When the elapsed time T3 is equivalent to or in excess of the given time $X3_2$, a "YES" branch is taken from decision branch 480 to step 490, which causes a termination of novel stimulus N1 presentations and a transmission of the "alarm" signal (as discussed above with regard to elements 34, 36, and 39 of FIG. 2) in step 500. Step 500, in turn, causes a suspension (i.e., "stop") in the operation of the apparatus in step 510, which step corresponds to step 240 in FIG. 4. Operation does not resume after a "stop" without a manual reset (i.e., reset 42 of FIG. 2), as discussed above with regard to parent or care provider intervention.

The "alarm" signal and "stop" functions of the present invention are included to ensure that operation does not continue indefinitely in the continued presence of criterion responding. Such an "alarm" signal is interpreted as an indication of actual subject distress, requiring intervention by the parent or care provider. Hence, in the event of actual subject distress, the operation of the present invention is suspended in favor of the exigencies of the "distress" situation. Freedom for such vocal behavior to occur without any suppressive countermeasures protects the subject child from any harmful effects, with respect to any functions of the present invention.

With regard to FIG. 4, the foregoing discussion clearly describes each breakpoint (i.e., mode change) in FIGS. 3A-3C where branching occurs relative to the branch indications of FIG. 4.

Many modifications and variations to the foregoing embodiments of the present invention are within the skill level of one of ordinary skill in the art without departing from the broader conceptual spirit and features of the present invention. For example, various component reinforcer mechanisms may be added to a basic unit as optional features without departing from the scope of the present invention.

Other indicators, such as tones or lights, may signal the subject child of a change among the various modes. For example, a change from mode 1 operation to mode 2 operation may be signaled by the cessation of a tone and/or a light. That is, the tone and/or light would operate continuously during mode 1 operation. A change from mode 1 operation to mode 2 operation may be contingent upon a duration measure in addition to the magnitude measure, discussed above. That is, such change may be contingent upon vocal behavior which is equal to or above the threshold TH for a predetermined period of time. The presentations of "positive reinforcer" R1 may be separated by a number of "short" intervals immediately following a change from mode 2 operation to mode 1 operation. That is, "long" intervals between presentations of "positive reinforcer" R1 at this breakpoint may be undesirable.

(i) A response dependent schedule of reinforcement may be used instead of or in addition to the variable time (VT) schedule of mode 1. For example, vocal responses which fall within a specified audible range—said specified audible range being below the threshold TH—may be reinforced according to a variable interval (VI) schedule. Under such a schedule, the first such response which occurs after the passage of some variable time interval will be reinforced. However, other responses (i.e., nonvocal responses) together with appropriate monitoring means as well as other schedules of reinforcement may be used to achieve the desired reinforcement density in mode 1.

(ii) Reinforcer R2 may be a stimulus (e.g., the above mentioned tones and lights) correlated with a return to mode 1 operation. Such a stimulus may be referred to as a conditioned positive reinforcer.

The foregoing discussion of schedule parameters (i.e., modes) is intended to be comprehensive with respect to the current state of the art as it applies to the present methodology (i.e., nondetrimental reduction of infant "crying" behavior). However, given the paucity of relevant data in the literature on infant "crying" behavior, certain questions and contradictions remain, which can be resolved only via the rigor of further scientific investigation. For example, under some circumstances, intermittent stimulation is known to increase arousal levels in infants. Accordingly, mode 1 operation may serve to increase the arousal level of the subject child, thereby eliciting "crying" behavior—rather than "reinforcing" the occurrence of behaviors which are incompatible with "crying" behavior. Similarly, the presentation of a novel stimulus as a consequence of a response is known, under some circumstances, to reinforce such responding. Accordingly, mode 3 operation may serve to reinforce "crying" behavior, rather than to elicit a pause in such behavior.

Also, the three modes herein described may be used separately or in different combinations of two's, other than the all-combined (modes 1, 2 and 3) combination described for FIGS. 3A-3C. For example, modes 1 or 2 might be used alone, or the combinations $\frac{1}{2}$, $\frac{2}{3}$ and $\frac{1}{3}$ might be used.

All such modifications and variations are intended to be included in the present invention, which is set forth in more particularity by the appended claims.

What is claimed is:

1. A method for nondetrimental reduction of infant "crying" behavior, comprising the steps of:
   establishing a criterion response defined as vocal behavior equal to or above a predetermined audible level;
   continuously monitoring the vocal behavior of said infant;
   presenting an intermittent "positive reinforcer" (R1) to said infant noncontingently during absence of said criterion response;
   suspending said presentation of said intermittent "reinforcer" (R1), when said monitored vocal behavior is in accord with said criterion response; and
   presenting a positive reinforcer (R2) to said infant contingent upon the cessation of vocal behavior in accord with said criterion response for at least a predetermined time period $X2_1$.

2. A method as in claim 1, wherein said presenting intermittent "reinforcement" (R1) step further includes a step of presenting said intermittent "reinforcer" (R1) only in the absence of said criterion response for at least a predetermined time period $X1_1$.

3. A method as in claim 2, wherein said presenting intermittent "reinforcement" (R1) step further includes a step of presenting said intermittent "reinforcer" (R1) for only a predetermined time period $X1_2$ for a given presentation of said intermittent "reinforcer" (R1), thereby mitigating satiation and habituation effects on said infant.

4. A method as in claim 1, wherein said presenting positive reinforcement (R2) step further includes a step of returning to said step of presenting intermittent "positive reinforcer" (R1) if said presentation of positive reinforcer (R2) results in the cessation of criterion responding for at least a predetermined time period $X2_2$.

5. A method as in claim 1, further comprising the step of presenting nondetrimental, novel stimuli to said infant, if said presenting positive reinforcement (R2) step fails to result in the cessation of criterion responding within a predetermined time period $X3_1$, said novel stimuli intended to elicit an "orienting response" from said infant which will result in cessation of said criterion responding.

6. A method as in claim 5, wherein said presenting novel stimuli step further includes the step of terminating presentation of said novel stimuli if cessation of said criterion responding has not occurred within a predetermined time period $X3_2$.

7. A method as in claim 6, wherein said presenting novel stimuli step further includes the step of returning to said step of presenting positive reinforcer (R2) if said presentation of novel stimuli results in cessation of said criterion responding for at least said predetermined time period $X2_1$.

8. A method as in claim 1, wherein said positive reinforcers (R1 and R2) are selected from a group of positive reinforcers including recordings of maternal heartbeats, recordings of placental sounds, changing patterns of shapes and colors, and movement of small physical objects such as rotatable mobiles.

9. A method as in claim 5, wherein said novel stimuli include at least one of flashing lights and relatively brief audible sounds.

10. A method for reduction of behavior of a particular type of a subject comprising the steps of:
establishing a criterion response;
continuously monitoring said subject behavior to determine presence or absence of said criterion response;
presenting a first "positive reinforcement" (R1) noncontingently during absence of said criterion response;
suspending said first "positive reinforcement" (R1) contingent upon presence of said criterion response; and
presenting a second positive reinforcement (R2) step contingent upon cessation of criterion responding.

11. A method as in claim 10, wherein said first "positive reinforcement" (R1) step includes presenting an intermittent "positive reinforcer" to maintain the absence of said criterion responding by said subject.

12. A method as in claim 10, wherein said second positive reinforcer (R2) step includes presenting a positive reinforcer to reinforce the cessation of said criterion responding by said subject.

13. A method as in claim 10, further comprising the steps of:
presenting novel stimuli to said subject, contingent upon the presence of said criterion responding for at least a predetermined time period;
suspending said presentation of said novel stimuli and reverting to said second positive reinforcement (R2), contingent upon the cessation of said criterion responding for a predetermined time period; and
terminating said presentation of said novel stimuli, upon failure to effect the cessation of said criterion responding for said predetermined time period within another predetermined time period.

14. An apparatus for reduction of behavior of a particular type of an infant, comprising:
microphone means for sensing vocal behavior of said infant;
comparator means, responsive to said microphone means, for indicating if said sensed vocal behavior is equal to or above a predetermined audible level; and
control means, responsive to said comparator means, for presenting positive reinforcers to said infant only during absence of sensed vocal behavior equal to or above said predetermined audible level.

15. An apparatus as in claim 14, wherein said control means further includes a reinforcement mechanism for selectively presenting said positive reinforcers.

16. An apparatus as in claim 15, wherein said reinforcement mechanism includes at least one of a controllable cassette recorder for playback of prerecorded sounds, a flashing light mechanism for presenting kaleidoscopic or patterned stimuli and a rotatable mobile.

17. An apparatus as in claim 14, wherein said control means further includes timer means for presenting said positive reinforcers only when absence of sensed vocal behavior equal to or above said predetermined audible level has been continuously monitored for at least a predetermined time period.

18. An apparatus as in claim 17, wherein said control means further includes first mode means for presenting said positive reinforcers as a defined "positive reinforcer" (R1) only when absence of sensed vocal behavior equal to or above said predetermined audible level has been continuously monitored for at least said predetermined time period.

19. An apparatus as in claim 18, wherein said control means further includes third mode means for presenting novel stimuli to said infant to elicit an "orienting response" to induce cessation of sensed vocal behavior equal to or above said predetermined audible level after occurrence of sensed vocal behavior equal to or above said predetermined audible level for a given period of time.

20. An apparatus as in claim 19, further comprising transmitter and receiver means for indicating, remotely from said control means, which of said mode means is presently functioning.

21. An apparatus as in claim 17, wherein said control means includes second mode means for presenting said positive reinforcers as a defined positive reinforcer (R2) contingent upon cessation of sensed vocal behavior equal to or above said predetermined audible level for at least a second predetermined time period, after an indication of sensed vocal behavior equal to or above said predetermined audible level, and for suspending said presentation of said positive reinforcer (R2) contingent upon renewed indication of sensed vocal behavior equal to or above said predetermined audible level.

22. An apparatus as in claim 21, wherein said control means further includes third mode means for presenting novel stimuli to said infant to elicit an "orienting response" to induce cessation of sensed vocal behavior equal to or above said predetermined audible level, after said suspension of presentation of said positive reinforcer (R2).

23. An apparatus as in claim 21, further comprising transmitter and receiver means for indicating, remotely from said control means, which of said mode means is presently functioning.

24. An apparatus for reducing the probability of abusive behavior directed toward an infant by a care provider, comprising:
variable audible level means for establishing a minimum audible level of "crying" by said infant which may give rise to said abusive behavior toward said infant;

microphone means for monitoring vocal behavior of said infant;

comparator means, responsive to said microphone means, for comparing said monitored vocal behavior with said minimum audible level; and control means, responsive to said comparator means, for presenting a schedule of reinforcement to said infant intended to maintain absence of monitored vocal behavior equal to or above said minimum audible level.

25. An apparatus as in claim 24, wherein said control means further includes first mode means for presenting an intermittent "positive reinforcer" (R1) during absence of monitored vocal behavior equal to or above said minimum audible level.

26. An apparatus as in claim 25, wherein said control means further includes second mode means for presenting a positive reinforcer (R2) contingent upon cessation of monitored vocal behavior equal to or above said minimum audible level.

27. An apparatus as in claim 26, wherein said control means further includes third mode means for presenting novel stimuli to elicit an "orienting response" to induce the cessation of monitored vocal behavior equal to or above said minimum audible level, contingent upon presence of monitored vocal behavior equal to or above said minimum audible level for a predetermined time period.

28. An apparatus as in claim 27, wherein said control means comprises a microprocessor programmed to perform all recited functions of said control means.

* * * * *